United States Patent [19]

Di Giorgio et al.

[11] Patent Number: Plant 7,125

[45] Date of Patent: Jan. 23, 1990

[54] CARNATION NAMED DIGIDARK

[75] Inventors: Antonio Di Giorgio; Renato Di Giorgio, both of San Remo, Italy

[73] Assignee: Laboratoire de Physiologie Vegetale, La Londe-Les Maures, France

[21] Appl. No.: 295,370

[22] Filed: Jan. 10, 1989

[51] Int. Cl.[4] ..... A01H 5/00

[52] U.S. Cl. ..... Plt./73

[58] Field of Search ..... Plt./73

*Primary Examiner*—Robert E. Bagwill

*Attorney, Agent, or Firm*—Charles W. Rummler

[57] ABSTRACT

A new and distinct standard carnation cultivar particularly distinguished by its very large blooms of a Cardinal Red coloration borne singly on long, strong, upright stems from a plant producing at least four stems, emitted near the ground, and having a height of about 110 cm. at eight months of growth. The plant having a vigorous, upright and well-branched growth habit with moderately abundant foliage and a recurrent blooming habit producing flowers profusely during the Spring, Midseason and Fall blooming periods.

1 Drawing Sheet

BACKGROUND OF THE NEW PLANT

This new carnation variety originated as a seedling of a hybrid developed by us in 1984 at our nursery at San Remo, Italy, by crossing two varieties selected from our collection of carnations maintained at our nursery for breeding purposes. This particular seedling was selected for progation because of its very strong Cardinal Red flowers produced on long, strong, upright stems of a tall plant having excellent characteristics for commercial propagation for cut flower production. This selected seedling was propagated by us by means of cuttings at our San Remo, nursery with very satisfactory results and because the plant appeared to have very good commercial possibilities, we continued propagation of this new plant at our San Remo nursery through several successive generations by cuttings, which proved to us that the novel characteristics of the selected seedling would be retained from generation to generation and its homogeneity for commercial propagation could be assured.

This new carnation variety is now being propagated for commercial purposes by means of cuttings as well as by in-vitro propagation procedures, at Establissments Barberet et Blanc, Laboratoire de Physiologie Vegetale, at 83250 La Londe-Les Maures, France.

DESCRIPTION OF THE DRAWING

This new standard carnation variety is illustrated by the accompanying photographic drawing, which shows several blooming stems with flowers as well as a single stem having a bud at a stage just prior to dividing of the sepals for opening of the full bloom, the color rendition being as nearly true to that herein specified as is reasonably possible to obtain by professional photographic procedures.

DESCRIPTION OF THE NEW PLANT

The following is a detailed description of our new carnation variety based upon observation of plants grown in greenhouse, as well as outside, at San Remo, Italy, and also at La Londe-Les Maures, France. The color designations stated herein are according to the R.H.S. Colour Chart published by The Royal Horticultural Society of London, England.

THE PLANT

Origin: Seedling.

Parentage:

*Seed parent.*—Variety No. 75.

*Pollen parent.*—Variety No. 8. Both parents are identified in our breeding records maintained in our nursery office at Via Villetta 41, 18038 San Remo, Italy.

Classification:

*Botanic.—Dianthus caryophyllus.*

*Commercial.*—Standard Carnation.

Form: An erect bush having at least four stems emitted near the ground.

Height: In average, about 110 cm. at eight months of growth.

Main stem: Less than 15 cm. tall due to pinching.

Branching: This plant is well branched.

Growth: Vigorous, upright and rigid.

Foliage:

*Quantity.*—Moderately abundant.

*Number of leaves.*—Less than 200.

*Leaf size.*—In average, about 15.8 cm. long and about 0.8 cm. wide (at seventh node).

*Leaf shape.*—Oblong with entire margins.

*Texture.*—Leathery.

*Color.*—Both upper and under sides, 189-A/B.

*Ribs and veins.*—Hardly noticeable.

*Leaflets.*—None.

THE BUD

Size: Large.

*Diameter.*—Averages about 3.5 cm.

*Length.*—Averages about 3 cm.

Shape: Generally ovoid.

Rate of opening: Normal.

Color of Petals:

*When sepals first divide and when petals begin to unfurl.*—Cardinal Red.

Sepals:

*Number.*—Five or six.

*Shape.*—Generally ovoid with acute apex and joined together at their lower parts.

*Character.*—The sepals are hooded over the bud and curl back when the flowers open.

*Color.*—Inside, 145-D and 187-D. Outside, 145-B, 143-C and 187-D.

*Striae.*—Longitudinal.

Calyx:

*Shape.*—Bell-shaped.

*Size.*—Large.

*Aspect.*—Smooth.

*Splitting.*—A little splitting sometimes occurs.

Flower stem:

*Length.*—About 78 cm., in average.

*Character.*—Erect and rigid.

*Color.*—189-A/B.

THE FLOWER

Blooming habit: Recurrent and profusely in the Spring, Midseason and Fall blooming periods.

Size of flower: Very large.

*Diameter.*—Averages 8.5 cm.

*Depth.*—Averages 6 cm.

Borne: Singly on a long, strong and upright stem.

Shape: When bloom first opens, high-centered. When bloom matures, dome-shaped.

Petalage:

*Number of petals.*—Averages 89.

*Arrangement.*—Imbricated.

*Form.*—Fan-shaped with rounded and deeply serrated margins.

*Texture.*—Leathery.

*Aspect.*—Velvety.

*Color.*—Both outer and inside petals: Body — 53-B with glints of 185-A. Base — Greenish. Reverse side — 185-A/185-B.

*Petaloids.*—Number: Less than 13. Size: Smaller than petals. Color: Cardinal Red, the same as the petals.

Flower stem: About 78 cm. (cut at tenth node).

Color: 189-A/B.

Character: Upright with good strength.

Discoloration after full bloom: Very little.

Persistence: The flower petals hang on and dry.

Fragrance: Light.

Lasting quality: As a cut flower, at least ten days in vase keeping.

REPRODUCTIVE ORGANS

Stamens:

*Number.*—Eight to thirteen.

*Arrangement.*—Around the ovary.

*Anthers.*—Size: Less than 4 mm. Color: Garnet.

*Filaments.*—Length: Averages about 2.8 cm. Color: Garnet.

Pistils:

*Number.*—Two.

*Styles.*—Length: About 2 cm. Color: Garnet.

*Stigma.*—Color: Garnet.

*Character of ovaries: Ribbed.*

Our new variety most nearly resembles Lonbulog (U.S. Plant Pat. No. 5,965). Compared with Lonbulog, however, our new variety has a larger flower and a wider calyx. The flower has serrated petals and a deeper color.

We claim:

1. The new and distinct standard carnation variety, substantially as herein shown and described, particularly characterized by the Cardinal Red coloration of its very large blooms and the profuse production of flowers on strong, upright stems having moderately abundant foliage during the recurrent flowering periods of the plant.

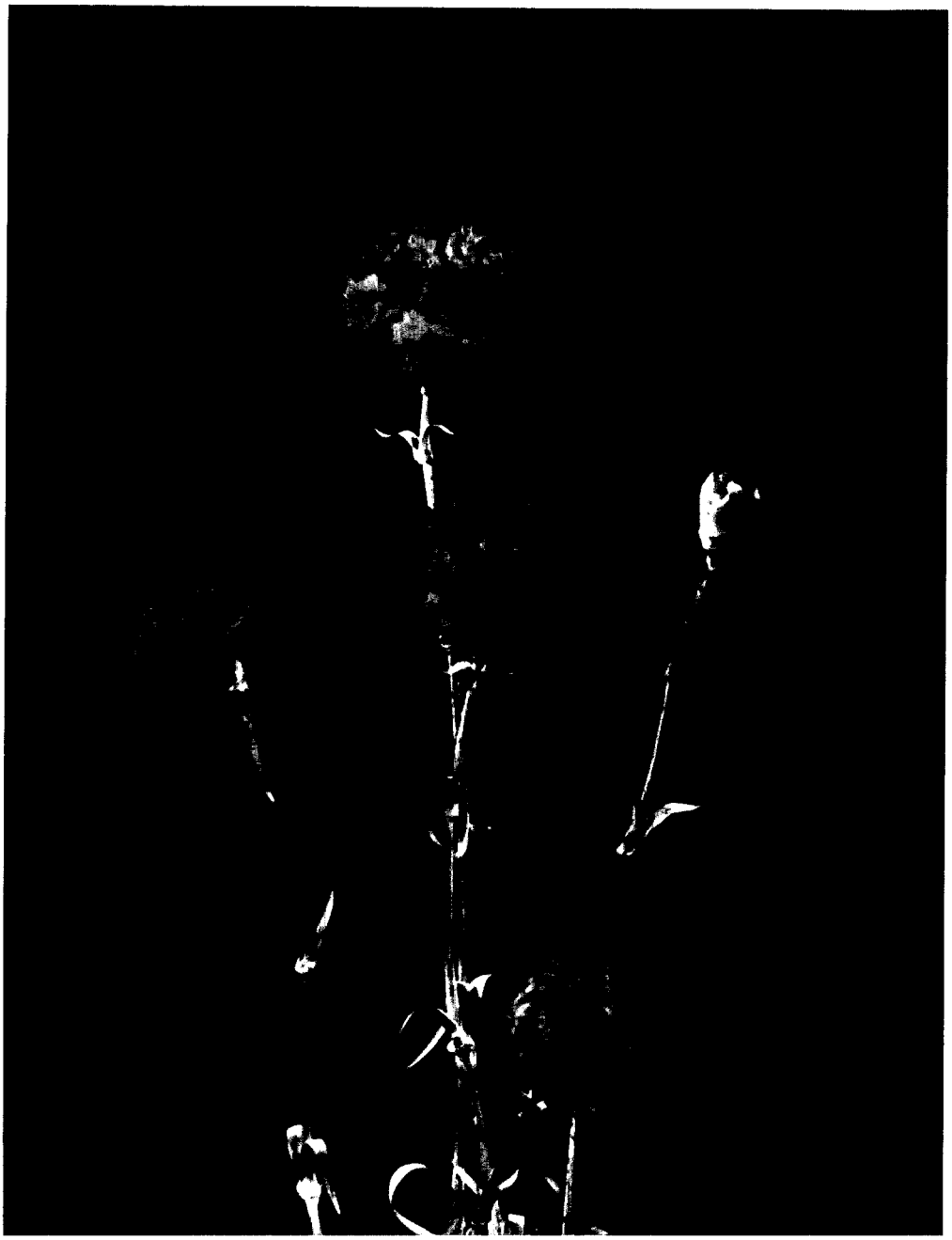

* * * * *